United States Patent [19]
Streit et al.

[11] Patent Number: 5,883,512
[45] Date of Patent: Mar. 16, 1999

[54] CHECKING HEAT EXCHANGER TUBES WITH AN EDDY-CURRENT INTEGRITY TEST

[75] Inventors: Klaus Streit, Roettenbach; Franz Ammann, Erlangen, both of Germany

[73] Assignee: Siemens Aktiengesellschaft, Munich, Germany

[21] Appl. No.: 740,255

[22] Filed: Oct. 25, 1996

[30] Foreign Application Priority Data

Dec. 14, 1995 [DE] Germany .................. 195 46 788.4

[51] Int. Cl.$^6$ .......................... G01N 27/72; G01N 27/82; G01R 33/12; B24C 1/00
[52] U.S. Cl. .............................................. 324/220
[58] Field of Search .................. 324/220, 225, 324/228, 262, 219, 234, 238

[56] References Cited

U.S. PATENT DOCUMENTS 4,306,914  12/1981  Long ..................................... 324/228
5,134,367   7/1992  Griffith et al. .

OTHER PUBLICATIONS

Siemens AG Power Generation Group, XXI Reunion Annual, "Effective Heat Exchanger Tube Cleaning by Advanced Mechanical Methods" by Roumiguiére et al..

*Primary Examiner*—Walter E. Snow
*Attorney, Agent, or Firm*—Herbert L. Lerner; Laurence A. Greenberg

[57] ABSTRACT

A method for checking heat exchanger tubes of metallic material includes drying inner surfaces of the heat exchanger tubes. A compressed air-abrasive mixture is then led through the heat exchanger tubes. An eddy-current integrity test of the heat exchanger tubes is then performed.

8 Claims, No Drawings

CHECKING HEAT EXCHANGER TUBES WITH AN EDDY-CURRENT INTEGRITY TEST

BACKGROUND OF THE INVENTION

FIELD OF THE INVENTION

The invention relates to a method for checking heat exchanger tubes made of metallic material.

Heat exchangers and especially heat exchanger tubes disposed in the heat exchanger are regularly checked with nondestructive test methods as to their condition. One of those test methods is the eddy-current integrity test which is known as such. That test makes it possible to recognize even very minor defects or damages in a tube, for example cracks, which penetrate only slightly into the tube wall and which cannot yet cause a leak. It is necessary to recognize such small cracks at an early stage, especially for heat exchangers which are part of a nuclear power plant, in order to prevent a leak.

It was found that the accuracy of the defect detection in the eddy-current integrity test decreases during the course of the operating time. Furthermore, it was found that in the course of the operating time the heat exchange also decreases.

SUMMARY OF THE INVENTION

It is accordingly an object of the invention to provide a method for checking heat exchanger tubes, which overcomes the hereinafore-mentioned disadvantages of the heretofore-known methods of this general type and with which defect recognition can be improved in an eddy-current integrity test and heat transfer in the heat exchanger can be maintained.

With the foregoing and other objects in view there is provided, in accordance with the invention, a method for checking heat exchanger tubes of metallic material, which comprises drying inner surfaces of heat exchanger tubes; then leading a compressed air-abrasive mixture through the heat exchanger tubes; and then performing an eddy-current integrity test of the heat exchanger tubes.

This achieves the advantage of arriving at an improvement of the defect recognition in an eddy-current integrity test of the heat exchangers in a surprising manner. Furthermore, a worsening of the heat exchange in the heat exchanger is avoided or reversed. Defects or damages to the heat exchanger tubes can be recognized at an early stage and the heat exchanger remains serviceable longer than usual because of a constant or improved heat conductivity of the heat exchanger tubes.

The method according to the invention significantly reduces the noise level in an eddy-current integrity test and this test leads to clearly more reliable results. Furthermore, the heat conductivity of the heat exchanger tubes is improved and the risk of material corrosion on the heat exchanger tubes is even reduced. These advantages can be attributed to the fact that undesired residues can be sufficiently and easily removed from the inner surface of the heat exchanger tubes. Such residues are formed during the course of the operating time of heat exchangers and show a different chemical composition and a different structure.

In order to obtain the above-mentioned advantages, a chemical cleaning or decontamination, which would necessitate a removal of secondary waste, does not have to be carried out in the heat exchanger tubes.

In accordance with another mode of the invention, the inside of the heat exchanger tubes, for example, is dried by evacuating and/or circulation of dried air.

In accordance with a further mode of the invention, the compressed air-abrasive mixture is, for example, lead through the heat exchanger tubes for a period of between 1 minute and 10 minutes.

In accordance with an added mode of the invention, the pressure of the compressed air, which is a component of the compressed abrasive mixture, can be, for example, between 0.1 MPa (1 bar) and 1 MPa (10 bar) when entering into the heat exchanger tubes.

In accordance with an additional mode of the invention, the abrasive which is a component of the compressed air-abrasive mixture, can be formed of granular, spherical, cubic and/or parallelepiped particles. The abrasive can also be a granulate.

In accordance with yet another mode of the invention, the abrasive is formed, for example, of glass, corundum, high-grade steel, ceramic and/or the material of the heat exchanger tubes. It is also possible for a defined mixture of abrasives to be used which is formed of different materials.

In accordance with yet a further feature of the invention, the diameter of the particles of the abrasive is, for example, between 100 $\mu$m and 1000 $\mu$m.

In accordance with a concomitant mode of the invention, the particle diameter of the abrasive is especially between 150 $\mu$m and 300 $\mu$m.

Other features which are considered as characteristic for the invention are set forth in the appended claims.

Although the invention is described herein as embodied in a method for checking heat exchanger tubes, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the description of specific embodiments.

The method according to the invention can be carried out in an especially reliable manner with the examples for drying and for treating the heat exchanger tubes.

The method according to the invention attains the advantage of ensuring that not only the heat conductivity of the heat exchanger tubes remains but also that the noise level during an integrity test with eddy-currents is clearly decreased, whereby a reliable early recognition of even small surface defects in the heat exchanger tubes is made possible.

We claim:

1. A method for checking heat exchanger tubes of metallic material, which comprises:
   drying inner surfaces of heat exchanger tubes;
   then leading a compressed air-abrasive mixture through the heat exchanger tubes; and
   then performing an eddy-current integrity test of the heat exchanger tubes.

2. The method according to claim 1, which comprises carrying out the step of drying the inner surfaces of the heat exchanger tubes by at least one of evacuation and circulation of dried air.

3. The method according to claim 1, which comprises leading the compressed air-abrasive mixture through the heat exchanger tubes for a period of between 1 minute and 10 minutes.

4. The method according to claim 1, which comprises adjusting a pressure of the compressed air in the compressed air-abrasive mixture when entering the heat exchanger tubes to be between 0.1 MPa (1 bar) and 1 MPa (10 bar).

5. The method according to claim 1, which comprises forming the abrasive in the compressed air-abrasive mixture of particles having a shape selected from the group consisting of granular, spherical, cubic and parallelepipedal.

6. The method according to claim 1, which comprises forming the abrasive in the compressed air-abrasive mixture of a substance selected from the group consisting of glass, corundum, high-grade steel, ceramic and material of the heat exchanger tubes.

7. The method according to claim 1, which comprises forming the abrasive in the compressed air-abrasive mixture of particles having a diameter between 100 $\mu$m and 1000 $\mu$m.

8. The method according to claim 1, which comprises forming the abrasive in the compressed air-abrasive mixture of particles having a diameter between 150 $\mu$m and 300 $\mu$m.

* * * * *